(12) United States Patent
Zank et al.

(10) Patent No.: US 8,570,038 B2
(45) Date of Patent: Oct. 29, 2013

(54) LONG RANGE DETECTION OF EXPLOSIVES OR CONTRABAND USING NUCLEAR QUADRUPOLE RESONANCE

(75) Inventors: Paul A. Zank, Brookline, NH (US); Peter A. Ketteridge, Amherst, NH (US); John T. Apostolos, Lyndeborough, NH (US); Candice L. Brittain, Nashua, NH (US)

(73) Assignee: R.A. Miller Industries, Inc., Grand Haven, MI (US)

( * ) Notice: Subject to any disclaimer, the term of this patent is extended or adjusted under 35 U.S.C. 154(b) by 524 days.

(21) Appl. No.: 12/957,893

(22) Filed: Dec. 1, 2010

(65) Prior Publication Data

US 2012/0161762 A1 Jun. 28, 2012

Related U.S. Application Data

(60) Provisional application No. 61/337,067, filed on Jan. 29, 2010.

(51) Int. Cl.
*G01V 3/00* (2006.01)
*G01R 33/44* (2006.01)

(52) U.S. Cl.
USPC ........... 324/309; 324/300; 324/307; 324/318; 702/23; 600/410

(58) Field of Classification Search
USPC ........................... 324/300–322; 600/407–464
See application file for complete search history.

(56) References Cited

U.S. PATENT DOCUMENTS

| | | | |
|---|---|---|---|
| 3,641,440 A | 2/1972 | Bush | |
| 4,513,292 A | 4/1985 | Bowman | |
| 5,594,338 A * | 1/1997 | Magnuson | ..................... 324/318 |
| 5,608,321 A | 3/1997 | Garroway et al. | |
| 6,900,633 B2 | 5/2005 | Sauer et al. | |
| 7,170,288 B2 | 1/2007 | Fullerton | |
| 7,352,180 B2 | 4/2008 | Manneschi | |
| 7,394,250 B2 | 7/2008 | Itozaki et al. | |
| 7,417,440 B2 | 8/2008 | Peschmann et al. | |
| 7,511,496 B2 | 3/2009 | Schiano | |
| 7,768,262 B2 | 8/2010 | Schiano | |
| 7,888,646 B2 | 2/2011 | Breit et al. | |
| 8,463,557 B2 * | 6/2013 | Apostolos et al. | ............... 702/23 |
| 2004/0196036 A1 * | 10/2004 | Lai | ................................ 324/300 |
| 2005/0241639 A1 | 11/2005 | Zilberg | |
| 2006/0012371 A1 | 1/2006 | Laubacher et al. | |
| 2006/0122484 A1 | 6/2006 | Itozaki et al. | |
| 2006/0232274 A1 | 10/2006 | Shilstone et al. | |

(Continued)

FOREIGN PATENT DOCUMENTS

| | | |
|---|---|---|
| EP | 838036 | 10/2006 |
| WO | 2006071198 | 7/2006 |

*Primary Examiner* — Melissa Koval
*Assistant Examiner* — Emily Chan
(74) *Attorney, Agent, or Firm* — McGarry Bair PC (57) ABSTRACT

Nuclear quadrupole resonance substance detection at a distance is provided by crossed or overlapping high frequency beams in which the frequency of one of the beams is offset with respect to the frequency of the other beam by an amount equal to the resonant frequency of the non-linear material to be detected. The presence of energy at the offset frequency within the overlapping beams pumps any non-linear material within the overlapping beams to cause stimulated emission which is detected, in one embodiment, utilizing a network analyzer, along with correlation of the detected stimulated emission signature with a library of signatures for predetermined substances.

17 Claims, 8 Drawing Sheets

(56) References Cited

U.S. PATENT DOCUMENTS

| | | | |
|---|---|---|---|
| 2007/0153974 A1* | 7/2007 | Smith | 378/57 |
| 2007/0221863 A1 | 9/2007 | Zipf | |
| 2008/0309339 A1 | 12/2008 | Chisholm et al. | |
| 2009/0041187 A1 | 2/2009 | Peschmann et al. | |
| 2009/0085565 A1 | 4/2009 | Fullerton | |
| 2010/0022009 A1 | 1/2010 | Yaniv | |
| 2010/0212401 A1 | 8/2010 | Crowley et al. | |

* cited by examiner

Fig. 9

LONG RANGE DETECTION OF EXPLOSIVES OR CONTRABAND USING NUCLEAR QUADRUPOLE RESONANCE

RELATED APPLICATIONS

This Application claims rights under 35 USC §119(e) from U.S. Application Ser. No. 61/337,067 filed Jan. 29, 2010, the contents of which are incorporated herein by reference.

FIELD OF THE INVENTION

This invention relates to the use of nuclear quadrupole resonance (NQR) for long range detection of molecules and more particularly to the use cross product modulation associated with non-linear materials to generate stimulated emissions from explosives or contraband at large distances from a detection point, with the material irradiated with two high frequency beams offset in frequency by the frequency of the spectral line of the material to be detected.

BACKGROUND OF THE INVENTION

As discussed in the co-pending Patent Application corresponding to Provisional Application 61/299,652 filed Jan. 29, 2010, it is possible to detect the presence of explosives or contraband utilizing nuclear quadrupole resonance. In this application a detected substance is irradiated with low frequency energy in the 0.1-5 MHz band which corresponds to a spectral line of the material to be detected. The resulting stimulated emission is indicative of the presence of the material, with the material being irradiated utilizing a terminated balanced transmission line.

The range of such systems from the balanced transmission line is limited. Also, the transmission lines are relatively long and in some cases are provided in the form of a balanced transmission line grid or matrix.

While it is possible to detect materials of interest at short distances from the grid or transmission line, long range detection techniques are required.

There is therefore a necessity for being able to detect the stimulated emission spectra of explosives or contraband at large distances from a detection point. For instance, it is desirable to be able to scan a crowd and detect the presence of explosives or contraband carried by an individual at some distance from a detection point.

It is also desirable for instance to be able to detect explosives or contraband carried in vehicles which may be at some distance from a detection point; and to do so in a stealthy manner.

It is noted that for 0.1-5 MHz, the antennas associated with such frequencies are exceedingly large. Also long are the terminated balanced transmission lines which need to be in place prior to the detection of explosives or contrabands.

Moreover, in an application when one is seeking to drive a vehicle down a road, one wants to be able to detect the presence of explosives ahead or beside the vehicle. Vehicles in general cannot conveniently carry antennas that are resonant at the low MHz frequencies very easily because of their size. There is therefore a need to provide a compact portable system for detecting explosives or contraband at a distance without having to use antennas whose quarter wavelengths are on the order of hundreds of feet.

In short, there is a need for long range detection of the stimulated emission from material caused by the absorption of 0.1-5 MHz energy.

SUMMARY OF INVENTION

Rather than attempting to directly project 0.1-5 MHz energy at a distance, in the subject invention two overlapping high frequency beams in the gigahertz range are pointed towards a given area using microwave dishes or directional antennas and the like, with the difference in frequency $F_2-F_1$ between the two beams being the frequency associated with the spectral line or the so-called resonance frequency of the material to be detected.

It is a property of non-linear materials when radiated with energy of two frequencies that cross product modulation occurs. It has been found that cross modulation products exist at the location of the material when illuminated by the two beams and includes amongst other products the $F_2-F_1$ spectralline energy.

The non-linear material phenomena is explained as follows:

It will be noted that the material responds to the beat or difference frequency between the present electromagnetic fields. When the beat frequency is correct, the spin states are pinned to single spin levels and are maintained over the normally thermally driven random equilibrium spin states. However when a noise event does occur, or in a stochastically driven series of relaxations, it stimulates a neighboring spin state to relax and a chain reaction can occur, very much like a laser gain material with its excited meta stable state relaxation, or nuclear fission chain reactions.

Note, nonlinearity involves the forced extension of the material dipole into a magnitude where the restoring forces become asymmetric and relax with richer spectral components. This process creates meta stable populations of spin coherence among the analyte present which then undergoes a noise triggered stimulated relaxation.

As will be appreciated the beams can be from two different antennas, the beams of which cross in space. Alternatively, the same antenna can he used to produce both beams so they are co-located and create the opportunity for $F_2-F_1$ energy to propagate along the entire length of the beam.

By offsetting the frequencies of the two beams by exactly the amount of the spectral line in question, one can create energy at the appropriate spectral line and project it into any material that exists within the crossed or overlapping beams. This in turn causes a stimulated emission from the material which can be detected.

Thus, rather than using very large antennas and very high power to create energy at large distances, in the subject invention narrow beams of electromagnetic energy in the gigahertz range offset by the spectral line frequency overlap to cause cross modulation products to be generated in the illuminated material, with the resultant stimulated emission being detected by an antenna tuned to the particular spectral line frequency of interest. These receive antennas do not need to be large and can, in one embodiment, include a tuned whip antenna. The frequency to which the receive antenna is tuned can be varied as for instance by using an antenna tuner so as to present a very low VSWR at the particular spectral frequency involved.

Additionally, unlike the case where the transmitted energy is at the same frequency as the received energy, necessitating a directional coupler, here no directional coupler is required due to the large frequency spread between the transmitted and received signals.

Moreover, and as discussed in the aforementioned patent application, the frequency of the energy injected into of the material can be swept so that the signature of stimulated emission returns can be matched to or correlated with known signatures of the material of interest. As a result, stimulated emissions from the material of interest can be distinguished from background or emissions from other material.

In summary, nuclear quadrupole resonance substance detection at a distance is provided by crossed or overlapping high frequency beams in which the frequency of one of the beams is offset with respect to the frequency of the other beam by an amount equal to the resonant frequency of the non-linear material to be detected. The presence of energy at the offset frequency within the overlapping beams pumps any non-linear material within the overlapping beams to cause stimulated emission which is detected, in one embodiment, utilizing a network analyzer, along with correlation of the detected stimulated emission signature with a library of signatures for predetermined substances.

BRIEF DESCRIPTION OF THE DRAWINGS

These and other features of the subject invention will be better understood in connection with the Detailed Description, in conjunction with the Drawings, of which.

DETAILED DESCRIPTION

Prior to describing the subject invention and by way of further background, in the early 1900s, not long after Einstein published his equations on thermal equilibrium, individuals realized that there were likely to be resonances at very low frequencies for atoms and molecules and that these resonances would occur because if one emits a photon of exactly the correct frequency, the material will absorb this photon, store it for some amount of time and then get rid of the absorbed energy. It is has been found that in nature the molecules which absorb such energy always fall to a lower energy state.

One of the ways for the material to emit energy is through spontaneous emission where a photon of exactly the same energy that is impinging on the material is thrown off in a random direction at random times.

The second way of getting rid of the energy absorbed by the material is through process of stimulated emission in which a photon arrives at exactly the appropriate energy, gets near the molecule, stimulates the molecule and when the molecule drops to the lower energy state it emits a photon that is exactly in phase with the original photon.

The energy that is thrown Off either in spontaneous emission or stimulated emission results in an exceedingly narrow spectral line. In fact the line is generally considered to be a single line that exists at a given wavelength or frequency. It is noted that the material only has one choice assuming that the material is pumped at its lowest energy state, raising the energy within the molecule such that the only way that it can release its energy is to emit a photon of that exact energy.

Nuclear quadrupole resonance has been utilized in the past to detect the presence of specific molecules, including explosives. Explosives generally involve the use of nitrogen or nitrogen bonded with other elements. When nuclear quadrupole resonance was utilized in the past, it was used to detect the presence of molecules due to the molecular elements that are bonded together such that the molecules absorb energy at for instance as many as eight different energy levels or spectral lines. It turns out that at least three of the energy levels tend to be prominent, although in some materials there are upwards of all eight energy levels for one bond. If one has many bonds there may be many dozens of spectral lines. In order to detect the presence of a molecule one usually is looking to pump energy right at the top of one of the spectral lines and look for energy coming back at the same frequency.

Prior Pulsed Coil Systems

It is noted that prior nuclear quadrupole resonance techniques can be likened to looking into a headlight to find a 1% response.

In the prior pulsed systems, a pulsed coil nuclear quadrupole resonance detection system to detect molecules requires upwards of 100 kilowatts of energy coupled to a very high Q tuned coil having for instance a Q of 80 or better. If there is any offset in terms of the frequency of the incident radiation or if the coil tuning was not precise, then any emissions from the molecule will be lost in the clutter.

First and foremost in the prior art pulsed coil nuclear quadrupole resonance techniques, it was only with difficulty that one could in fact detect any response. One of the reasons is because the coil exhibits a large dwell time after which one looked for a response.

If one did not wait, the incoming radiation would swamp the detectable results. In order to eliminate this problem, those in the past used a pulsed source and then waited for a response after the trailing edge of the pulse. Prior systems thus pumped pulsed energy into a coil with the target material at the center of the coil. Thereafter the material would absorb energy and then the prior systems would listen for the spontaneous decay.

The problem with spontaneous decay is that at thermal equilibrium a spontaneous photon happens only once for every two million stimulated photons. Thus, in terms of detecting spontaneous decay, one is at an extremely difficult power disadvantage. Secondly, the spontaneous decay might happen over several tens of milliseconds which means that the instantaneous power levels at any point in time are very low. For spontaneous decay using a pulsed coil nuclear quadrupole resonance, the problem is that one is working with very few photons and further they are stretched out over time. This means that one has to use huge amounts of power to overcome these problems, often in the nature of kilowatts of energy. Moreover, because one is looking at very low signal strength the coil is made with a very high Q. This means that the coil couples well with the environment, that in turn means that the coil picks up a great deal of background noise.

Pulsed coil nuclear quadrupole resonance detection systems have been marginally cost effective and their power density has exceeded human safe limits.

More specifically, taking RDX as an example, the bandwidth of the RDX resonance is about 400 hertz. This means that the associated decay time or relaxation time is on the order of 2.5 milliseconds. If one were to sweep the frequency through the resonance as one approaches the resonant frequency, what happens is that one excites the nucleus of the nitrogen atom. When the nucleuses are excited they go into an upper state and then as one sweeps by the frequency there is a population inversion in these nuclei at which time they start to decay.

If one utilizes a long CW pulse what would happen is that one would see a periodicity of absorption and emission. When the CW pulse is turned on, the molecule goes into the excited state but then relaxes through stimulated emission. What would happen utilizing a CW signal is that one would see a series of absorptions and emissions that would occur every 2.5 milliseconds.

For RDX, assuming a pulsed coil system, one must use a pulse width of about half a millisecond because the pulse has to decay down fast enough so that the spontaneous emission can be observed.

Thus in the past a relatively short pulse of CW energy was used to enable listening for the response. However, in order to be able to detect the response at all, a very high Q coil was required. High Q coils have an excessive relaxation time. As a result, in order to provide for the ability to listen when driving a very high Q coil at half a millisecond one has to have other circuitry to quench the coil as fast as possible so as to be able to listen to the return, typically in terms of a little hiss that comes off after irradiation with the pulse.

Thus, in the prior systems one had to have exceedingly large kilowatt sources of 3 MHz energy in order to obtain enough of a response, and then had to pulse the source so as to be able to stop it and quench it in time to be able to detect the minuscule response that would occur.

Having the high Q coil further was complicated by the fact that one could not frequency sweep a sample because the high Q coil resonates at only one frequency.

This for instance precludes the ability to distinguish between the detection of multiple spectral lines to be able to distinguish the spectral response of the target molecules from the spectral responses from uninteresting molecules.

Also, when using a high Q coil one has to use an exceedingly large amount of shielding to make the system safe for use around people, as well as having to actively quench the coil.

Moreover, when pumping 1 kilowatt into a coil, the presence of the system is very easy to detect. Thus, terrorists could avoid screening knowing that such a detection system was in operation.

Note that the pulsed coil system detects spontaneous not stimulated emissions. Spontaneous emissions are not coherent and one obtains the square root of the power coming back.

Thus, in the past it has been virtually impossible to provide a workable system that would reliably and safely detect dangerous amounts of explosive material hidden on a human.

Short Range NQR Systems

As discussed in a Patent Application by Paul A. lank and John T. Apostolos, entitled Method and Apparatus For Sensing The Presence Of Explosives, Contraband and Other Molecules Using Nuclear Quadrupole Resonance, based on Provisional Patent Application 61/299,652, filed on even date herewith and incorporated herein by reference, as part of the subject invention, it has been found that the spectral lines of interest especially for explosives are in the 100 KHz to 10 MHz range. A particularly interesting explosive is RDX which has a spectral line in the 3 to 4 MHz range, as does sodium nitrate.

However if one is seeking to detect stimulated or emission or spontaneous emission at 3 MHz, the wavelength of the returns is incredibly long, in some cases corresponding to the size of a building. Moreover, the photons that are emitted in either spontaneous or stimulated emission represent very little energy. For instance, a red photon carries an energy of about 3.5 electron volts, with detectable radiation being one or two millionths of 3.5 electron volts. The result is that photons emitted from the molecules are virtually undetectable. One of the reasons is that in order to detect single photons one is faced with thermal background that overwhelms the detection process. In order to achieve any type of result, one pumps large numbers of photons into the target material such that for every milliwatt second an extraordinary number of photons are involved.

If the photons are at the appropriate frequency they are absorbed and only when the frequency exactly corresponds to a resonance line does the molecule start absorbing the photons. Thus it is quite important that the frequency source utilized in the nuclear quadrupole resonance measurements be extremely precise and stable.

If one performs a frequency sweep, the emission that comes back is on the order of 1% of the energy that impinges on the molecule.

Improved NQR System

Rather than using a single terminated balanced transmission line discussed in a patent application by Paul A. Zank and John T. Apostolos, entitled Method and Apparatus for Sensing the Presence of Explosives, Contraband and other Molecules Using Nuclear Quadrupole Resonance, filed on even date herewith and incorporated herein by reference, in an application based on Provisional Application Ser. No. 61/299,652, an array is provided for nuclear quadrupole resonance detecting systems in which an array of loaded or terminated balanced transmission lines is used for wide area coverage. In one embodiment, side by side balanced transmission lines are simultaneously driven in phase with synchronous frequency swept signals. Each of the balanced transmission lines is fed with a low power swept frequency source and stimulated emissions are picked off with a directional coupler. For location, if a crossed grid array is used, the location of the sensed substance at a cross point as well as its existence can be sensed over a wide area. Alternatively, if a phase detector is used for each balanced line, the phase between outgoing and incoming signals translates to the location of the sensed substance, measured from the feedpoint of the balanced transmission line.

Note, rather than using the high power noise-prone pulsed coil system for detecting nuclear quadrupole resonance lines due to spontaneous emission, in the subject system stimulated emission is sensed. For stimulated emissions, the energy produced by the molecule is not spontaneous and it is not happening randomly. Rather, the emission that is seen in the stimulated emission is coming back exactly in phase with the incident radiation, namely a coherent response.

More specifically, a low power swept frequency source is used in combination with a probe in the form of a terminated balanced transmission line in which molecules including explosives, narcotics and the like that are located between the transmission line elements are detected. In the subject system the result of the absorption of the milliwatt/watt energy is picked off with a directional coupler or circulator so as to eliminate the transmitted energy from swamping the received energy. What is seen is the 1% stimulated emission coherent result that is exactly in-phase with the transmitted signal. It is the coherent in-phase relationship that permits integrating the weak signals into a detectable result.

As a result of utilizing the directional coupler the transmitted signal is rejected. Moreover, the utilization of a balanced transmission line essentially has a zero Q, this eliminating the background noise associated with the high Q coils. Moreover, since the transmission line is not resonant at any one frequency, a sample can be frequency swept or simultaneously irradiated with signals at multiple frequencies. Additionally, there is no frequency limit to the sweep frequency since there are no tuned circuits involved.

In one embodiment, the energy is step wise swept so as to be able to correlate the result with spectral lines of a known molecule while being able to reject returns from molecules having other spectral lines.

It has been found for explosives such as TNT, RDX and PETN and other molecules of interest that sweeping between 100 KHz and 10 MHz is enough of a sweep to discriminate against non-target materials. For instance, while one might be looking for the spectral lines associated with RDX, one would also like to be able to ignore the spectral lines of for other materials, or for that matter glycine which is present in a great many biologic materials.

In one embodiment of the improved NQR system, the system is typically operated at between 200 milliwatts up to 10 watts, making the system, much safer than the high power kilowatt pulsed coil nuclear quadrupole resonance systems. Moreover, quenching is unnecessary.

For robust detection of the stimulated emission, more than one spectral line can be considered as an indicator of the molecule. For instance, for RDX one might wish to look at two or three of the RDX spectral lines. If it turns out that glycine is present, and if in fact one of the RDX spectral lines share a spectral line with the glycine, then one could ignore the overlapping spectral line.

While scanning network analyzers can be utilized as frequency sources for the subject invention, due to the fact that the transmission line does not discriminate from one frequency to the next, it is possible to connect multiple frequency sources in parallel to feed the transmission line resulting in simultaneous evaluation of several frequencies.

It is also possible to use a pseudo-random number code pattern so that the system would be difficult to jam. Moreover, the low power system is hard to detect, obscuring the fact that any scanning is going on at all.

In one embodiment while one could scan from 100 KHz to 10 MHz, this type of scanning procedure wastes a large amount of time and is not necessarily beneficial. If one is only looking for specific resonance lines, the scanning can be scheduled to appropriately frequency hop, thus dramatically reducing scanning time.

Note that no single detection of a spectral line is used to declare the presence of the target material. Rather, the system desirably requires multiple hits in order to declare the presence of the target material.

It is also noted that the subject system looks at the stimulated emissions, as opposed to the spontaneous emissions, primarily because the spontaneous emissions are perhaps one two millionth of the power of the stimulated emissions. This is important because, as mentioned above, in determining the presence of a target molecule, one is seeing only 1% of the incident energy being returned.

Further, RDX resonances have a bandwidth of approximately 400 hertz, which as mentioned above, results in a decay time or relaxation time of about 2.5 milliseconds. Assuming a stepped sweep approach, the nucleus of the atoms making up the molecules are excited and when they go into the upper state, there is a population inversion in these nuclei, with the stimulated emission occurring immediately thereafter. Note that the stimulated atoms that have been inverted relax coherently such that there is a coherent response back to the probe. Because of the 2.5 millisecond relation time stepped sweeps would have to be adjusted accordingly.

Since there is no coil involved, one does not have to use quenching and since one uses a directional coupler to ignore the transmitted signal, one does not have to stop and listen in order to get adequate readings.

Moreover, a cancellation algorithm may be utilized in which the transmission line is observed without a sample between the transmission line elements during a calibration sweep. Thereafter, any material that is between the transmission line elements has results that are subtracted from the calibration sweep results. Thus, if there are any peculiarities in the analyzer or transmission lines, these peculiarities are subtracted out. As a result, steady state noise is nulled out.

The reason for the use of the transmission line is that it focuses all the energy between the two balanced leads or elements. Because a balanced transmission line is the world's worst antenna by design it does not leak energy to the environment, unlike a coil. Concomitantly, the transmission line does not receive interference from the environment, making the subject system an extremely quiet system.

The above NQR system is implementable in a number of different forms such as providing two spaced apart transmission line elements to either side of a gate or portal through which an individual is to pass. Such a portal may be an airport security checkpoint. Moreover, two pieces of copper pipe or copper tape may be placed on opposing walls down a corridor to form the transmission line, or the balanced transmission lines can be placed on a road to detect the passage of target material between the transmission line elements. Additionally, the transmission line could for instance be configured as opposed guard rails.

Considering for instance that a terminated balanced line contains two elements, one element is called a plus element and the other is called a minus element. The magnetic flux lines are in a plane perpendicular to the axis of the elements. In one configuration, a large area can be covered using a number of side-by-side plus/minus lines. For instance, these lines could be laid out in a carpet at an airport to track people carrying explosives on their person. Thus, one can monitor the transmission lines to be able to tell where someone carrying explosives is walking and to be able to track their path.

It will be appreciated that the subject system, by avoiding the high Q coil, also avoids the large amount of shielding necessary for public safety or the safety of those operating the equipment. Also, as mentioned above, there is no need to actively quench any part of the probe in order to be able to listen to the relatively small returns from the irradiated sample.

Rather than having to run a kilowatt into a coil, in the above NQR system successes have been reported at a 200 milliwatt level with excellent signal to noise ratios. Thus, there is the ability to operate at a 30 dB lower power levels than a pulsed coil. This means that the entire system can be run at low power. The result is that the above system does not interfere with magnetic media or people's safety and is very hard to detect any distance away from the test site. Thus, even standing a few feet beside the balanced transmission line one is not able to detect it. As a result, a person would not know that he or she is being monitored. Also, if a pseudo-random hopping schedule is utilized, detection of the presence of such a system is virtually impossible.

As will be appreciated, the conductors for the transmission lines could be for instance as large as a two inch pipe, or could in fact be flat transmission line elements. It is also noted that the termination resistance is equal to the impedance of the transmission line. In one embodiment, the space between the elements is about 2.5 to 3 feet, such that one could conveniently paint conductive stripes on opposing sides of a corridor; with the impedance being controlled by how tall the stripes are and how far apart the stripes are. For a corridor-sized installation one might have a conductive stripe on either side of the corridor that is 11 feet long and about a foot tall.

Also with larger areas one needs more power to create the flux density required. Thus if one considers a 12 foot long probe, this requires about 36 times as much power as a miniature probe. It is the power density (watts/meter$^2$) that remains constant.

Regardless, one can obtain adequate results in a corridor type situation with between 7, and 10 watts of power into the probe.

The amount of power required is dependant on how much material one is trying to detect and also the flux density that one is trying to excite it with, as well as how much integration time is available.

Small amounts of explosives can be carried on the person in the persons clothing, swallowed, or can even be surgically implanted, which would be virtually undetectable through a physical examination of the person and also through standard X-ray techniques. Thus for the creative or diligent terrorist, it may be of interest to provide pockets of the explosive within the body of the individual that could not be readily detected by present techniques.

It is noted that the maximum flux density given two spaced apart conductors is on a line between the two conductors, with the minimum being outside the transmission line. As one proceeds to the edge of the conductors, one obtains more flux density. However, the flux density does not very significantly in a direction normal to the plane between the two transmission line elements so it is possible to get reasonable coverage for a human sized object or even a truck sized object above the transmission line. Note that the transmission line impedance can typically be between 100 and 1,000 ohms which, is not critical. The critical component is the flux density, with the critical flux density being approximately 1 watt per meter$^2$.

With a flux density of less than 1 watt per meter$^2$, the signal-to-noise ratio is less for the same integration time. If the flux density is greater than 1 watt per meter$^2$, then the signal-to-noise ratio is improved because of the coherent signal. The result of the coherency is that the signal-to-noise ratio improves linearly with how much integration time is utilized.

Integration time refers to the collection of the results of multiple stimulated emissions over time. As a general rule, one has to dwell on the target Material for whatever is the inverse of the particular bandwidth involved. Bandwidths in the subject case are on the order of a 100 to 500 hertz which results in dwell times of between 1 and 5 milliseconds.

Of course, as mentioned above, one need not frequency hop in 1 to 5 millisecond intervals because there is no reason why one cannot monitor multiple lines simultaneously or even feed the lines with parallel-outputted frequency generators. In short if one were using three signal generators coupled to the same transmission line, one could sense three different spectral lines simultaneously.

Since an NQR system of the type described herein can sample multiple frequencies simultaneously this is considerably different from the pulsed coil nuclear quadrupole-resonance systems that tend to tune a coil for a specific frequency because of the need for the high Q. Thus, in the subject system one can track the results over the entire bandwidth utilizing the same balanced transmission. line probe.

As a result, the NQR system is capable of detecting an entire class of explosives; whether they are people-born or vehicle-born. Moreover, the NQR system may detect contraband such as narcotics, with many narcotics having very specific nuclear quadrupole resonance signatures. This includes cocaine and heroin.

With suitably stabilized oscillators in the form of for instance multiple network analyzers, one can digitally synthesize multiple frequencies simultaneously. Fast-Fourier transforms are then used to sort out the frequencies. In this case one piece of hardware can generate multiple frequencies simultaneously. This cuts down the time that the specimen has to be between the elements of the balanced transmission line, thus for instance to be able to detect somebody who is running with explosives.

For stepped frequency sweeps, one can allocate 5 milliseconds per frequency. If one is analyzing 10 spectral lines then one is doing so in 50 milliseconds. However, the problem is that there may be 40 or 50 different prominent explosives, all with different spectral lines, and hundreds of compounds that have spectral lines in the same region. Thus instead of processing 10 spectral lines, one might have to process 1,000 spectral lines. At 50 hertz, this corresponds to a dwell time of 5 seconds and necessitates synthesizing all frequencies of interest simultaneously.

In summary, in one NQR system stimulated emissions due to nuclear quadropole resonance are detected utilizing an array of terminated balanced transmission lines and directional couplers, thus to detect explosives, contraband, narcotics and the like that exist between the transmission line elements, as well as to locate detected substances. In one embodiment, a stepped frequency generator is utilized to provide a scan between 100 KHz and 10 MHz. In another embodiment, parallel frequency sources are in-phase coupled to the balanced transmission lines, either embodiment permitting correlation with expected spectral lines, with the frequency sources being low power so as to not create a safety hazard and so as not to interfere with radiation sensitive devices such as film or electronic circuits that are in the vicinity of the balanced transmission lines.

The Balanced Transmission Line NQR System

Figure 1:
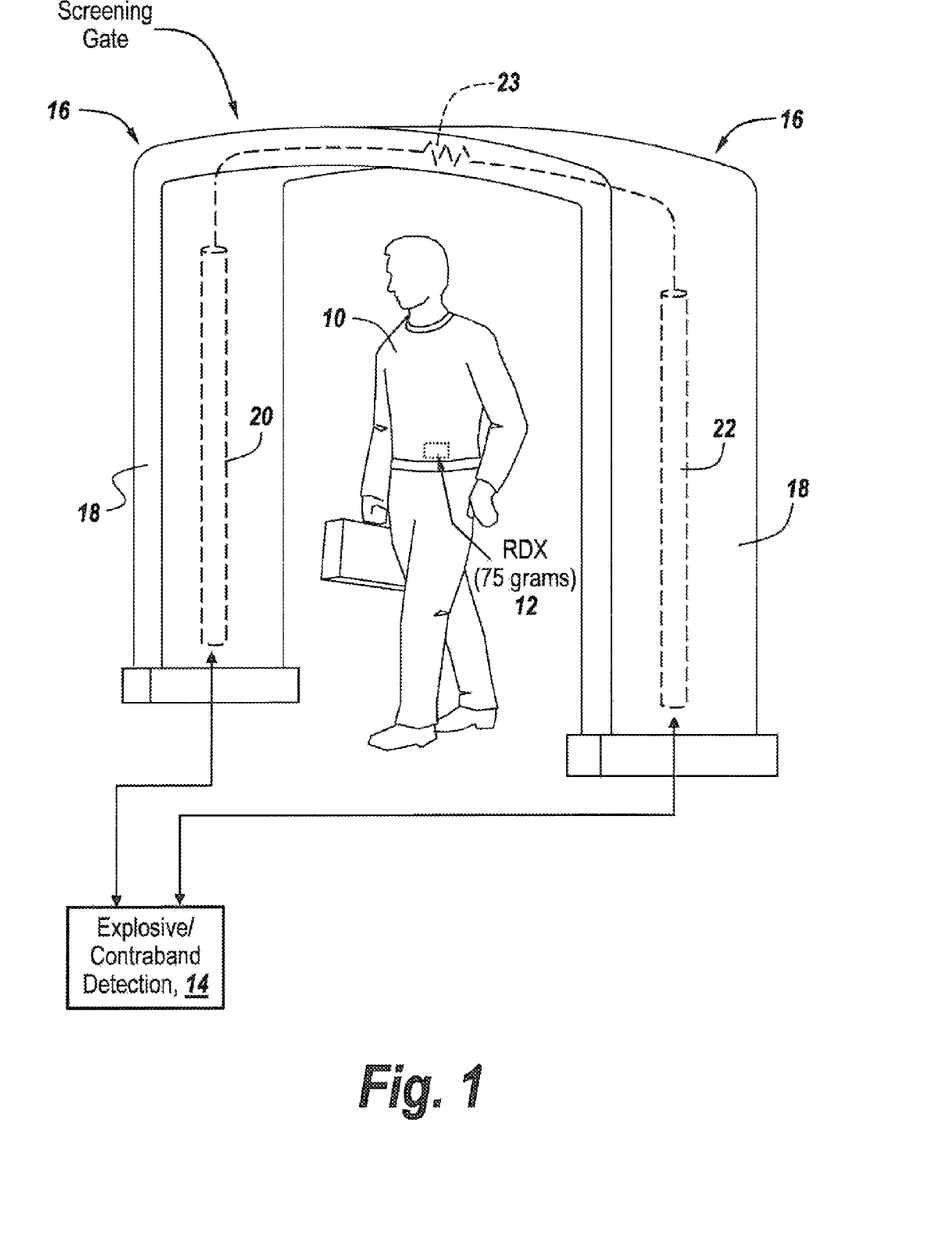
FIG. 1 is a diagrammatic illustration of one type of NQR system for the detection of an explosive hidden on an individual as the individual walks through a balanced transmission line coupled to an explosive/contraband detection unit that utilizes nuclear quadrupole resonance in which, in one embodiment, RDX spectral lines are detected to ascertain the presence of an explosive.

To further describe one embodiment of the above NQR system, and referring now to FIG. 1, an individual 10 may be carrying on his or her person some contraband or explosives 12 which may for instance may be secreted in his or her underwear, or could even be surgically implanted. One such explosive is RDX and it is the purpose of the subject invention to be able to detect explosives in as little quantity as 75 grams which is approximately about a fifth of a cup. Terrorists and the like are using more and more sophisticated ways of secreting explosives and/or contraband and a physical examination of the individual may not yield the presence of such explosives or contraband. Not only may the explosives or contraband be surgically implanted in the individual, they may be swallowed in bags and be held internally in the gut until such time as their "removal".

Present systems for detecting such explosives or contraband such as back scatter X-rays are not effective to detect such secreted items and the use of higher power radiation is counterindicated for safety reasons.

On the other hand, as shown in FIG. 1, an explosive or contraband detection system 14 utilizes nuclear quadrupole resonance in which swept frequencies are applied to a balanced and terminated transmission line 16 embedded in a screening gate or housing 18 in which the elements of the balanced transmission line 20 and 21 as well as load 23 are embedded in the gate. The balanced transmission line has no frequency to which it is tuned, such that the application of signals for instance between 100 KHz and 10 MHz may be applied due to the non-tuned nature of the probe which is comprised of elements 20, 21 and 23.

As will be seen, the power necessary to detect nuclear quadrupole resonance is in general below 10 watts and often as little as 200 milliwatts, due to the NQR explosives/contraband detection system which, inter alia, utilizes a directional coupler in the form of a circulator to cancel out the transmitted energy while receiving only the stimulated emission from the molecules in the target sample.

As used herein, the target sample 12 includes molecules having a particular recognizable spectrographic signature in which the spectral lines of the sample are recognizable when compared with the spectral lines generated through stimulated emission of all of the remaining molecules that surround the target sample.

For instance, glycine which is common in the human body has spectral lines that are distinguishable for instance from RDX spectral lines, with glycine in essence forming a background spectral signature which is to be distinguished.

While the subject invention will be discussed in terms of explosives, it is understood that the material under test may be molecules of any type having a known spectral signature. This includes contraband such as narcotics and other types of drugs such as heroin and cocaine which, due to the NQR system in one embodiment involving stepped and swept frequency transmission enables one to eliminate the spectral signatures of non-target materials while being able to single out the spectra of target materials.

Figure 2:
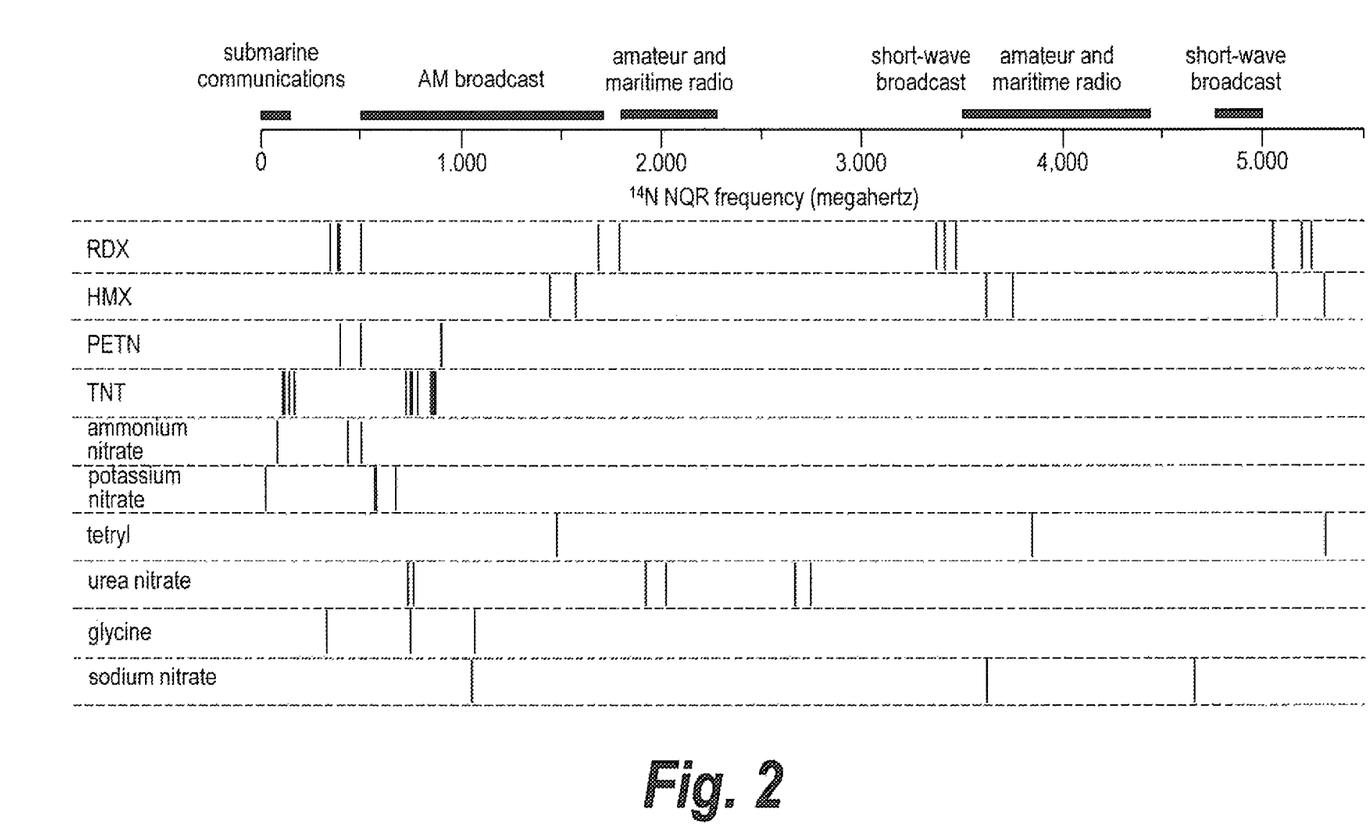
FIG. 2 is a graph showing the spectral signatures of a number of potential explosive materials indicating for RDX and HMX, a spectral signature in a 3-4 MHz range, with TNT indicating a spectral signature in the sub 1 MHz range as well as ammonium nitrate and potassium nitrate, with tetryl having a signature in the 3-4 MHz range and with urea nitrate having a spectral signature not only in the sub 1 MHz range but also in the 2-3 MHz range, noting that sodium nitrate has a very close spectral signature to one of the spectral lines of glycine.

Referring to FIG. 2, what is shown is a spectral chart for common explosive materials such as RDX, HMX, PETN, TNT, ammonium nitrate, potassium nitrate, tetral, urea nitrate and sodium nitrate, also as compared with the spectra of glycine.

What will be seen is that all of these materials have spectra between about 100 KHz and about 5 MHz, which spectra are detectable by the subject system. For instance, if one detects spectra of RDX in the 3-4 MHz band, this is clearly distinguishable from the glycine spectra which lie below 1.5 MHz.

Likewise one can distinguish PETN from RDX as well as being able to distinguish HMX from RDX due to the offset of the spectra of HMX in the 3-4 MHz band from the spectra of RDX.

Since the short range NQR system detects stimulated emission from all of the molecules in the sample between the balanced transmission lines, it is possible through correlation processing to be able to provide a probability of a match between the spectral lines of the target material as opposed to the spectral lines due from molecules that are not target materials and which constitute background.

Figure 3:
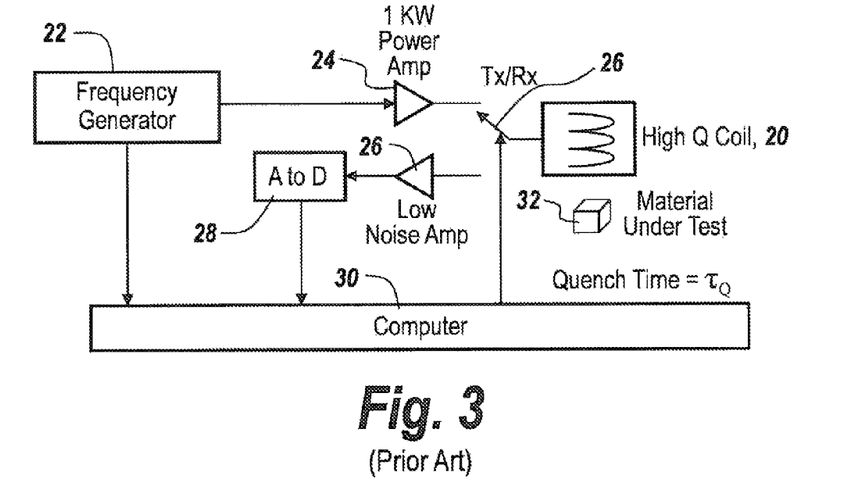
FIG. 3 is a diagrammatic illustration a prior art pulsed coil nuclear quadrupole resonance system illustrating the use of high power pulses and a high Q coil in which the system has a transmit-receive switch, the cycling of which depends on coil quench time.

Referring now to FIG. 3, what will be seen in the prior art pulsed coil nuclear quadrupole resonance system is the utilization of a high Q coil 20 which is driven from ¯a frequency generator 22, the output of which is amplified by an amplifier 24 to the 1 kilowatt level. The signal from the amplifier is switched via a transmit/receive switch 26 and is applied to the coil during a pulsed sequence, with switch 26 being returned to the receive position at which point the high Q coil 20 is coupled to a low noise amplifier 26, to an analog-to-digital converter 28 and thence to a computer 30 for measuring the spontaneous emission response from material under test 32.

In short, since the system described in FIG. 3 measures the spontaneous emission of the material under test and since in order to generate enough spontaneous emission high power was deemed to be necessary, the system of FIG. 3 is clearly not usable around human beings for safety reasons.

Moreover, in order to be able to eliminate the effect of the transmitted power with respect to the relatively low power of the receive signal, it was necessary to be able to quench high Q coil 20 so as to be able to see the return from the material under test. The quench time, $\tau_Q$ is problematic with respect to providing realtime measurements. It has been found that it is important to be able to provide circuitry to be able to quench high Q coil 20 in order to increase the pulse repetition frequency. However, the quench time when utilizing a high Q coil is problematic as mentioned above.

Moreover, the utilization of a high Q coil is problematic because it also collects background, which background can oftentimes obscure the results.

Figure 4:
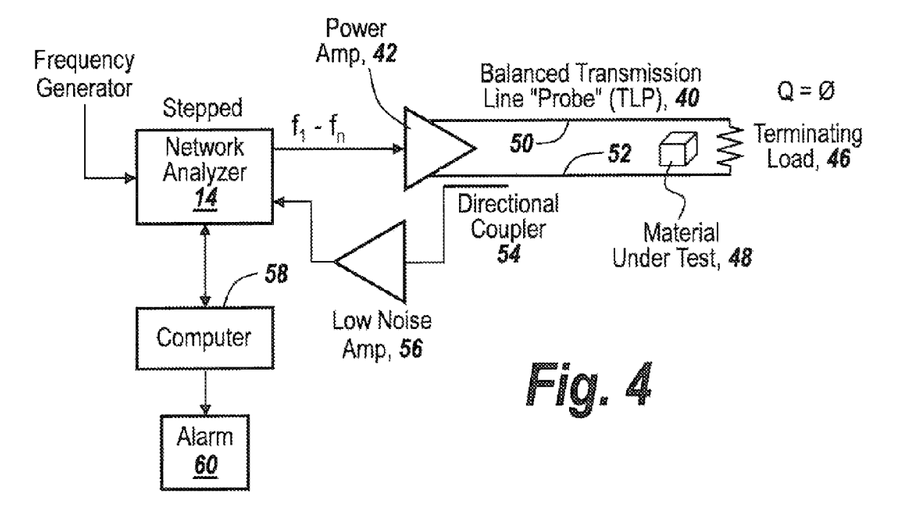
FIG. 4 is a diagrammatic illustration of the NQR system of FIG. 1 illustrating a stepped network analyzer functioning as a frequency source for generating a number of stepped frequencies which are amplified by a low power amplifier to less than 10 watts in one embodiment, with the amplifier being coupled to a balanced transmission line probe in which the transmission line is terminated in a load and in which a directional coupler is utilized to detect the stimulated emission from a material under test, unimpeded by the output power applied to the transmission line.

On the other hand and referring now to FIG. 4, a balanced transmission line probe 40 is coupled to a power amplifier 42 which amplifies a frequency generator 44 output, in one embodiment provided by a stepped network analyzer. The transmission line is terminated by a terminating load 46.

When a material under test 48 is placed between the balanced transmission line elements 50 and 52, it has been found that the stimulated emission from the material under test can be sensed utilizing a directional coupler 54 coupled to a low noise amplifier 56 which is in turn coupled back to the network analyzer 44 that detects a S21 the very low level stimulated response of the material under test. It is noted that network analyzer 44 is coupled to a computer 58 such that the returned signal can be processed and an alarm 60 activated if the material under test has a spectral signature match to that of a target material.

While it is possible to generate only one frequency corresponding to one the major spectral line of the target sample, it is useful to be able to scan frequencies for instance $f_1-f_n$ in order to detect the spectral lines of whatever materials might be between the elements of the balanced transmission line. Because the balanced transmission line has a Q of zero, not only is it possible to couple a wide frequency range of signals to the transmission line, the Q of zero also means that there is very little outside interference with respect to the signals that exist interior to the transmission line.

Moreover it has been found that while the flux densities vary at various positions between the transmission line elements, at least in the plane of the transmission line elements, locating a material under test above or below the plane of the transmission line elements does not materially affect the readings.

Figure 5:
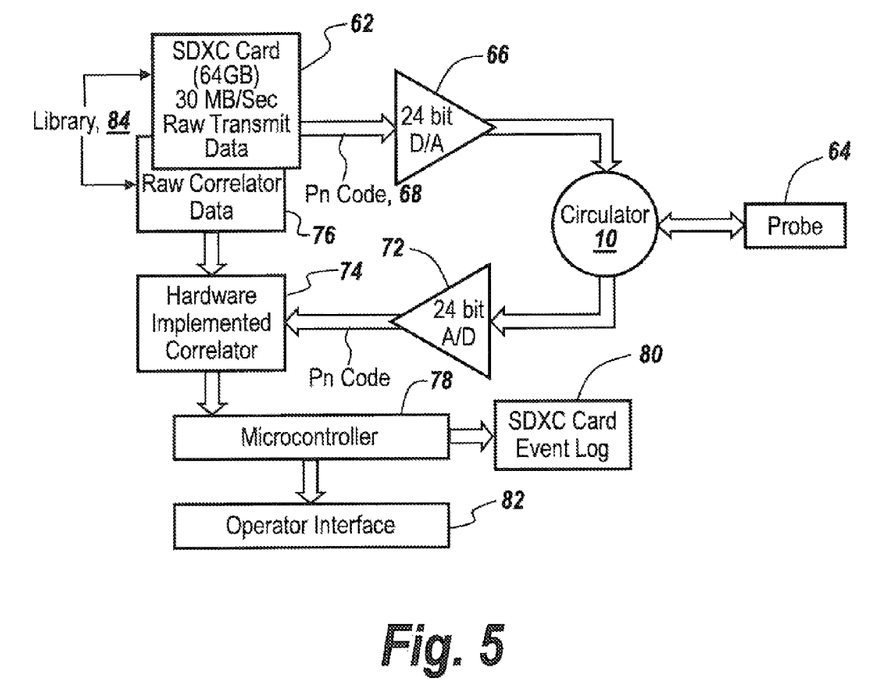
FIG. 5 is a block diagram of the subject system in which transmissions at various stepped frequencies are applied through a 24 bit digital-to-analog converter to a circulator that functions as a directional coupler, with the output of circulator being converted by a 24 bit A-D converter to correlate the returns with raw correlated data from a library, the output of the hardware-implemented correlator provided to a microcontroller for detecting the existence of a particular material present at the probe; Note that this system can be used to test several simultaneous frequencies simultaneously.

Referring to FIG. 5, in one embodiment an memory card (such as a SXDX 62 gigabyte card) having a 30 MB per second transfer rate may be utilized to generate the 100 KHz to 10 MHz signals that are coupled to probe 64 utilizing a 24 bit digital-to-analog converter 66 to which is applied a PN code 68 in one embodiment.

The utilization of a pseudo-random code is for defeating jamming, with the pseudo-random code being similar to that utilized in GPS systems for this purpose.

The input to the probe and the output from the probe are coupled to a circulator 70 which, as described above, completely eliminates the effect of the transmitted signal on the received signal, thereby to eliminate the problems of having to quench a high Q coil.

The output of circulator 70 is applied to a 24 bit analog-to-digital converter 72, with the receive PN code being applied to a hardware implemented correlator 74 that correlates the received stimulated emission information with raw correlator data 76 such that if there is a high correlation between the raw correlator data and the received data, microcontroller 78 may be used to drive memory card event log 80 and also provide an operator interface 82 alarm condition indicator.

Note that in terms of the generation of stepped frequency signals, a library 84 may be utilized that carries the spectral signatures of many types of target molecules. This results in the ability to generate a large variety of very narrow frequency signals which are applied to probe 64.

It will be appreciated that the frequency stability of the signal generator in the form of a network analyzer such as shown in FIG. 4 is critical due to the narrow nature of the spectral lines that are generated by the nuclear quadrupole resonance phenomena and the requirement of coherence.

Long Distance Detection

As described above, it is possible to detect substances utilizing nuclear quadrupole resonance when this substance is between the elements of a balanced transmission line. It is also possible to detect the presence of these materials when the substance is above or below the transmission line, at least to a distance of a few feet.

However in order to provide a long distance detection system, for instance for detecting materials carried by individuals in a crowd or for detecting materials that are in transit, it has been found that the stimulated emission occasioned by the injection of energy at a particular spectral line in a 0.1-5 MHz band may be generated when the material is physically situated in two crossed beams of high frequency energy, in which the energy in one beam is offset from the frequency of the other beam by exactly the spectral line of interest.

Figure 6:
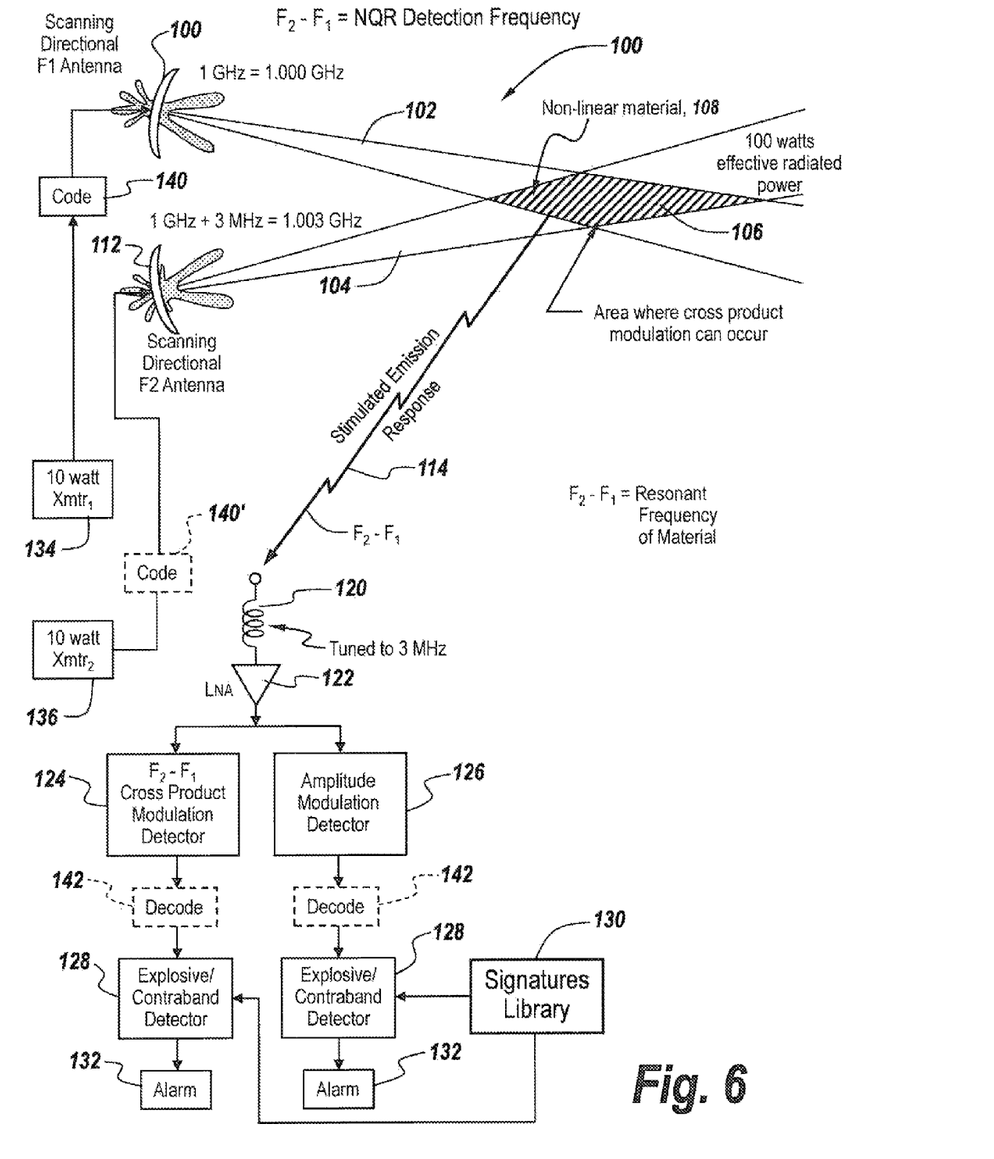
FIG. 6 is a diagrammatic illustration of the utilization of two high frequency beams, with one beam offset by the resonant frequency of the material to be detected, with the stimulated emission response from the non-linear material to be detected being detected by a tuned antenna, with the output supplied to a cross product modulation detector or an amplifier modulation detector, the outputs of which are coupled to respective contraband or explosive detectors coupled to a library of signatures.

Referring now to FIG. 6, a long distance NQR detection system 100 includes the projection of two beams 102 and 104 which cross in area 106, at which cross product modulation can occur. This is due to any non-linear material 208 that exists within the crossed beams.

In order to provide the energy that pumps the non-linear material, in the embodiment shown in FIG. 6 a pair of directional dish:antennas 110 and 112 are tuned to energy in the gigahertz range.

The energy projected by each of these dishes is such that assuming that the energy from dish 110 has a 1 GHz frequency then, the energy from dish 112 is offset in one embodiment by 3 MHz. The frequency of the resultant beam is therefore 1.003 GHz.

This offset in frequency causes a cross modulation product at the resonant frequency of the material to exist in area 106 due to the presence of 3 MHz energy. Due to the cross product modulation this 3 MHz energy then pumps any non-linear material within the crossed beams such that there is a stimulated emission response 214 from the non-linear material at $F_2-F_1$. Note that while there are numerous cross product modulation products, there will at least be one cross product modulation product at the exact spectral line of the material.

The stimulated emission response is detected in one embodiment by an antenna 120, which in one embodiment is a whip with a loading coil tuned to 3 MHz. It is therefore possible to provide a portable unit with a compact short whip and a tuned loading coil for the detection of the stimulated emission response. The output of antenna 120 is coupled to a low noise amplifier 122 which is in turn coupled either to a cross product modulation detector 124, or an amplitude modulation detector 126.

The outputs of detectors 124 or 126 are coupled to respective explosives/contraband detectors 128 of the type described hereinabove, each provided with a signatures library 130. Note, the stimulated emission signature is compared with signatures in library 130, with the output upon a match being coupled to an alarm 132.

In one embodiment one needs only 10 watt transmitters such as illustrated at 134 and 136 which provide CW energy at frequency $F_1$ and $F_2$. This virtually eliminates the possibility of damage to humans or animals in the beams.

To boost the signal-to-noise ratio of the system the output of either one of these two transmitters can be provided with a pseudo-random code generator 140 or 140' that impresses a pn code on the signal. As a result, when the stimulated emission response is detected, a pn decoder 142 is employed to decode the output of the cross product modulation detector or the amplitude modulation detector.

It is noted that the detection of the stimulated emission response is as described herein above for the NQR systems which utilize terminated balanced transmission lines.

It will be noted that the frequency offset of the signals from antennas 110 and 112 may be varied in a manner so as to sweep the frequencies of interest for whatever materials might be detectable in the crossed beams.

The result of utilizing the 10 watt transmitters is that the effective radiated power in the crossed beams is 100 watts, clearly sufficient to cause the stimulated emission in non-nuclear material within the area of the crossed beams without being harmful.

What will be appreciated is that one can mount the dishes 110 and 112 on a vehicle and provide a tuned receive antenna so that a mobile substance detection system can be easily deployed.

Figure 7:
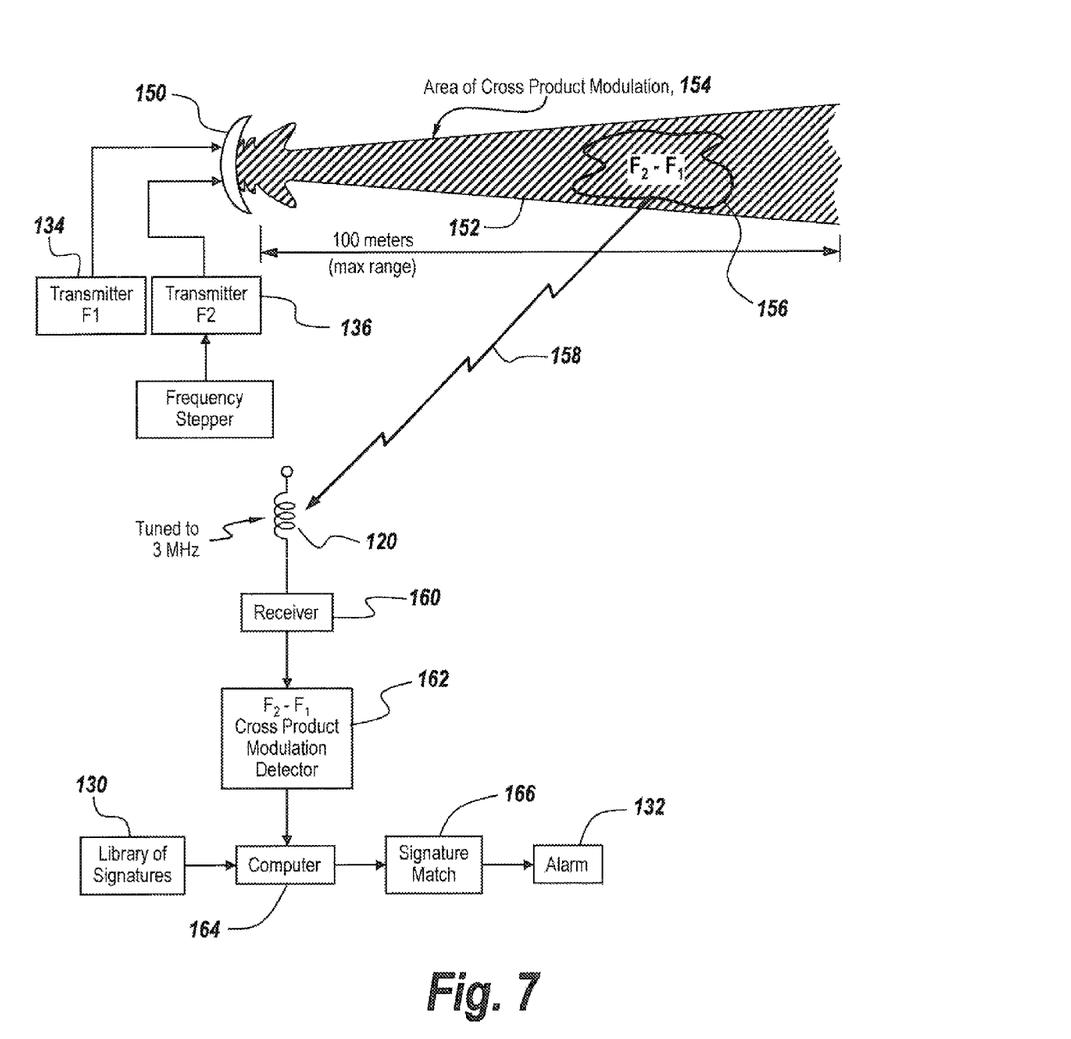
FIG. 7 is a diagrammatic illustration of the driving of a single high frequency antenna dish with two high frequency signals with one of the signals offset by the spectral line of interest, in which co-located beams are directed out from the antenna so as to project $F_1-F_2$ energy to any non-linear material that exists in the beam, and in which a tuned antenna at the spectral line is coupled to a receiver at a cross product modulation detector in turn coupled to a computer, coupled to a library of signatures for outputting an alarm when signature match occurs.

Referring now to FIG. 7, it will be appreciated that a single dish antenna 150 may be employed in the gigahertz range rather than using two dishes, since the frequency offset between the two transmitted signals $F_1$ and $F_2$ is minimal as far as dish tuning is concerned.

Thus, transmitter 134 and 136 may be coupled directly to the input to dish antenna 150. This results in a beam 152 which has an extensive region overlaps such that cross product modulation 154 can occur along the entire beam. Thus, any non-linear substance 156 within the beam will be pumped with the appropriate spectral line and have a stimulated emission response at $F_2-F_1$ as illustrated at 158, with the 0.1-5 MHz response being transmitted back to receive antenna 120. Receive antenna 120 is coupled for instance to a receiver 160, the output of which is then coupled to a cross product modulation detector 162, coupled in turn to a computer 164 provided with the aforementioned library of signatures 130. The result is to arrive at a signature match 166 which in turn activates alarm 132.

As can be seen from FIGS. 6 and 7, the maximum range for a 10 watt system is on the order of 100 meters, although the range varies proportionally to the amount of transmitted power, such that range may be extended to kilometers as opposed to meters.

Figure 8:
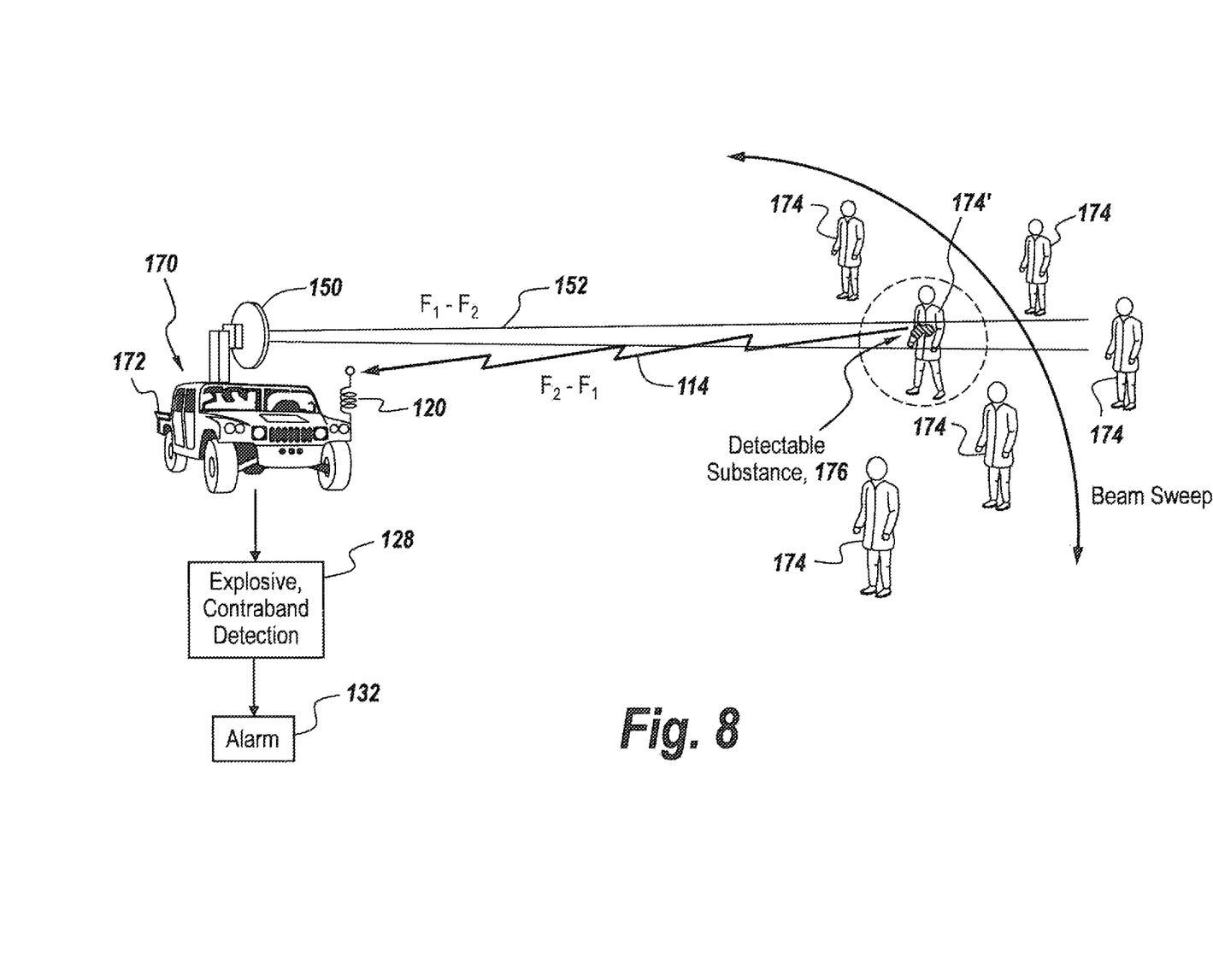
FIG. 8 is a diagrammatic illustration of the sweep of the beam of FIG. 7 embodiment to detect an individual having an explosive or contraband substance so as to be able to identify individuals carrying the material in question; and, FIG. 9 is a block diagram of the subject system in which a single side band up-converter is utilized to both provide $f_0+f_1-f_2$ to a summing node, as well as provide a 0.1-5 MHz swept signal to a network analyzer that receives not only the swept frequency signal from the up-converter but also the detected stimulated emission response to provide a S21 ratio signal to the computer used to detect the presence of a particular substance.

Referring now to FIG. 8, what this means is that a mobile NQR detection system 170 may be mounted on a vehicle 172, with antenna 150 mounted to the vehicle. Beam 152 which carries both frequencies $F_1$ and $F_2$ may be directed towards a crowd of individuals 174, with one of the individuals 174' carrying a detectable substance 176 on his or her person.

This substance for instance can be explosives or can be contraband, it being noted that if the contraband is swallowed the system will nonetheless result in the detection of the substance as long as the substance is within the narrow beam. The stimulated emission response $F_1-F_2$, here shown at 114, is again detectable by a tuned antenna 120 coupled to the system of FIG. 6 or FIG. 7.

Explosives or contraband detection 128 activates alarm 132 when such material is detected within beam 152.

While the subject system has been described in terms of a CW signal being projected into the material of interest, it is possible to provide a radar-like pulsed system such that the distance of the detected substance from antenna 150 may be determined by conventional distance measuring algorithms. The result is not only determining the direction to the detectable substance, but also its distance from the antenna.

Figure 9:
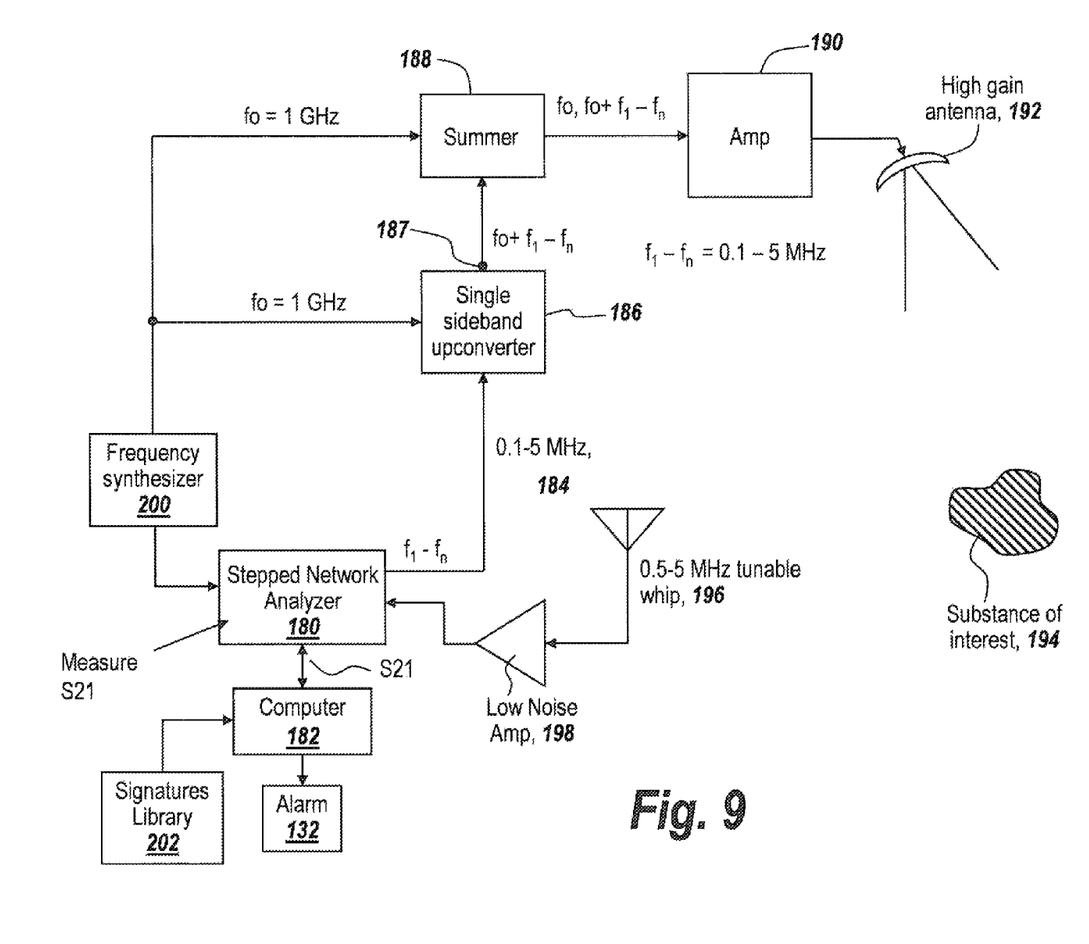

Referring to FIG. 9, in one embodiment a stepped network analyzer 180 may be coupled to a computer 182 and thence to alarm 132. Stepped network analyzer 180 is fed with a frequency source 200 such that the stepped network analyzer 180 outputs $f_1-f_n$ between 0.1-5 MHz to a single sideband up converter 186 that selects only the' upper sideband to mix with the $f_0=1$ GHz signal from frequency synthesizer 200. Note in an up conversion both sidebands are normally generated. However, a single sideband up conversion eliminates the lower sideband from being generated. The result is a unique $f_1-f_n$ sweep.

The output 187 of the single side band up converter is the fundamental $f_0$ one gigahertz signal plus the $f_1-f_n$ stepped offset. In one embodiment $f_1-f_n=0.1-5$ MHz is used to sweep all expected spectral lines.

This $f_0+f_1-f_n$ is applied to a summing junction 188 which, is also coupled to the one gigahertz fundamental signal $f_0$. The outputs of summing junction 188 are thus two signals, one at $f_0$ and the other at $f_0+f_1-f_n$ to provide the two beams.

The signals from summing junction 188 are applied to an amplifier 190 that is coupled to a high gain antenna 192 which irradiates any substance of interest 194 within the co-located beams. As before, tunable whip antenna 196 is employed to detect any stimulated emission, with its output applied to a low noise amplifier 198 that is coupled as an input to network analyzer 180. The output of the network amplifier is the S21 ratio for detecting the presence of a stimulated emission. Note, the network analyzer of FIG. 9 operates identically to the network analyzers described above when coupled to the frequency synthesizer. It will be appreciated that this frequency synthesizer may not only output f0, it may also be used as a clock so that the network analyzer can output $f_1-f_n$. This permits sweeping a relatively wide band so as to be able to identify the signatures of substances of interest.

Note also that computer 182 is provided with a signatures library 202 similar to the signature libraries discussed above.

What will be appreciated is that the S21 network analyzer output may be employed as a sensitive detector for detecting the stimulated emission from a substance of interest.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. Apparatus for long distance detection of a substance utilizing nuclear quadrupole resonance, comprising:
   at least one antenna for projecting two overlapping high frequency beams towards a given area;
   a pair of transmitters, one of said transmitters operating at a first frequency and the second of said transmitters operating at a different offset frequency, the offset being that associated with the resonant frequency of the substance to be detected, said transmitters being coupled to said at least one antenna;
   a receive antenna tuned to the resonant frequency of the substance;
   a cross product modulation detector coupled to said receive antenna for detecting the cross product modulation product corresponding to the resonant frequency of the corresponding substance; and,
   an explosive/contraband detector coupled to said cross product modulation detector for detecting a stimulated emission response of any of said substance in the overlapped beams, said explosive/contraband detector coupled to a signature library such that correlation between the stimulated response signature and at least one signature in the signature library is detected, such that if said substance exists in said crossed beams, the existence thereof will be ascertained.

2. The apparatus of claim 1, wherein said substance includes a non-linear material.

3. The apparatus of claim 1, wherein said at least one antenna is a directional antenna.

4. The apparatus of claim 3, wherein said at least one directional antenna includes a microwave dish.

5. The apparatus of claim 1, and further including a coding module between the outputs of one of said transmitters and said antenna for superimposing a code on the signal transmitted therefrom.

6. The apparatus of claim 5, and further including a decoding module coupled between said cross product modulation detector and said explosive/contraband detector.

7. The apparatus of claim 6, wherein said coding module and said decoding module are provided with identical codes, thereby to provide signal processing gain.

8. The apparatus of claim 1, wherein said explosive/contraband detector includes a network analyzer having an S21 output and wherein said stimulated emission response is measured in terms of said S21 output.

9. The apparatus of claim 1, and further including an amplitude modulation detector coupled to said receive antenna and substituted for said cross product modulation detector, said amplitude modulation detector coupled to said explosive/contraband detector.

10. The apparatus of claim 9, and further including a coding module between one of said transmitters and said at least one antenna and a decoding module coupled between said amplitude modulation detector and said explosive/contraband detector.

11. The apparatus of claim 1, wherein said at least one antenna includes two directional antennas that project crossing beams at a distance therefrom, said pair of transmitters being coupled to said directional antennas, whereby the existence of said substance in the area of the crossed beams can be ascertained.

12. The apparatus of claim 1, wherein said at least one antenna includes a single directional antenna, both of said transmitters being coupled to the input of said single antenna, said antenna providing two co-located beams which overlap along the length thereof.

13. The apparatus of claim 1, wherein said pair of transmitters include a frequency synthesizer, a frequency-stepped network analyzer coupled to said frequency synthesizer, said frequency synthesizer outputting clock pulses to said network analyzer, said network analyzer utilizing said clock pulses generate a stepped set of frequencies at which stimulated emissions are expected to occur;

a single sideband up converter coupled to said frequency synthesizer and network analyzer for outputting a signal corresponding to the fundamental $f_0$ output of said frequency synthesizer and said $f_0$ fundamental frequency plus the output signal of said stepped network analyzer, thus to output a frequency of $f_0$ plus the frequency from said stepped network analyzer;

a summing network coupled to said single sideband and up converter and said frequency synthesizer to output the $f_0$ fundamental frequency of said frequency synthesizer and the $f_0$ fundamental frequency plus the output frequency of said stepped network analyzer; and, an amplifier coupled to the summing network for amplifying the signal from said summing network, said amplifier being coupled to said at least one antenna.

14. The apparatus of claim 13, wherein said receive antenna is coupled town input of said network analyzer, the output of said stepped network analyzer being an S21 ratio indicative of the detection of stimulated emissions from said substance.

15. The apparatus of claim 14, and further including allow noise amplifier coupled between said receive antenna and said stepped network analyzer.

16. The apparatus of claim 1, wherein high frequency signals generated from said transmitters are in the gigahertz frequency range and wherein said offset is in the megahertz frequency range.

17. The apparatus of claim 16, wherein said megahertz frequency range is between 0.1 MHz and 5 MHz.

* * * * *

UNITED STATES PATENT AND TRADEMARK OFFICE
CERTIFICATE OF CORRECTION

| | | |
|---|---|---|
| PATENT NO. | : 8,570,038 B2 | Page 1 of 1 |
| APPLICATION NO. | : 12/957893 | |
| DATED | : October 29, 2013 | |
| INVENTOR(S) | : Paul A. Zank et al. | |

It is certified that error appears in the above-identified patent and that said Letters Patent is hereby corrected as shown below:

In the Claims:

Column 18, Claim 15, lines 33-34, read: "...and further including allow noise amplifier..."

It should read: "...and further including a low noise amplifier..."

Signed and Sealed this
Twenty-second Day of April, 2014

Michelle K. Lee
*Deputy Director of the United States Patent and Trademark Office*